United States Patent
Fujita et al.

(10) Patent No.: US 9,452,565 B2
(45) Date of Patent: Sep. 27, 2016

(54) ULTRASONIC HORN, WELDER PROVIDED THEREWITH, AND METHOD OF PRODUCING DISPOSABLE DIAPER USING ULTRASONIC HORN

(71) Applicant: ZUIKO CORPORATION, Settsu-shi, Osaka (JP)

(72) Inventors: Yukihiko Fujita, Osaka (JP); Hideyuki Nakamura, Osaka (JP)

(73) Assignee: ZUIKO CORPORATION (JP)

( * ) Notice: Subject to any disclaimer, the term of this patent is extended or adjusted under 35 U.S.C. 154(b) by 0 days.

(21) Appl. No.: 14/893,324

(22) PCT Filed: Jun. 13, 2014

(86) PCT No.: PCT/JP2014/065806
§ 371 (c)(1),
(2) Date: Nov. 23, 2015

(87) PCT Pub. No.: WO2014/200102
PCT Pub. Date: Dec. 18, 2014

(65) Prior Publication Data
US 2016/0107377 A1    Apr. 21, 2016

(30) Foreign Application Priority Data

Jun. 14, 2013  (JP) ................................. 2013-125941

(51) Int. Cl.
*B32B 37/00* (2006.01)
*B29C 65/00* (2006.01)
(Continued)

(52) U.S. Cl.
CPC ... *B29C 66/81431* (2013.01); *A61F 13/15739* (2013.01); *A61F 13/15747* (2013.01);
(Continued)

(58) Field of Classification Search
CPC ... B29C 65/08; B29C 65/083; B29C 65/086; B29C 65/087; B29C 65/088; B29C 65/7885; B29C 65/747; B29C 66/81431; B29C 66/0326; A61F 13/15585

USPC .................. 156/73.1, 580.1, 580.2
See application file for complete search history.

(56) References Cited

U.S. PATENT DOCUMENTS 6,482,291 B1    11/2002  Kume et al.
7,383,865 B2 *   6/2008  Umebayashi ..... A61F 13/15739
                                                156/350

(Continued)

FOREIGN PATENT DOCUMENTS

JP    2001-233309    8/2001
JP    2010-115283    5/2010

(Continued)

OTHER PUBLICATIONS

International Search Report.

*Primary Examiner* — James Sells
(74) *Attorney, Agent, or Firm* — Gerald E. Hespos; Michael J. Porco; Matthew T. Hespos (57) ABSTRACT

Provided is an ultrasonic horn, the output amplitude of which can be significantly increased. An ultrasonic horn includes an input-side end section that has an input surface that receives ultrasonic vibration, and an output-side end section having an output surface that outputs ultrasonic vibration to a sheet. The output-side end section has a dimension, in the length direction, over which a side edge portion of a front abdominal section and a side edge portion of a rear dorsal section can be welded in the longitudinal direction, and is branched in a width direction that is perpendicular to the length direction by a slit that extends in the length direction. A pair of surfaces of the output-side end section, positioned on both sides of the slit, functions as the output surface through which the ultrasonic vibration is output.

6 Claims, 8 Drawing Sheets

(51) Int. Cl.
*B29C 65/08* (2006.01)
*B29C 65/78* (2006.01)
*A61F 13/15* (2006.01)
*B29L 31/48* (2006.01)

(52) U.S. Cl.
CPC ......... *A61F13/15804* (2013.01); *B29C 65/08* (2013.01); *B29C 65/086* (2013.01); *B29C 65/7885* (2013.01); *B29C 66/0326* (2013.01); *B29C 66/1122* (2013.01); *B29C 66/232* (2013.01); *B29C 66/431* (2013.01); *B29C 66/7294* (2013.01); *B29C 66/81435* (2013.01); *B29C 66/81465* (2013.01); *B29C 66/82263* (2013.01); *B29C 66/8322* (2013.01); *B29C 66/83511* (2013.01); *B29C 66/83541* (2013.01); *A61F 2013/15821* (2013.01); *B29C 66/433* (2013.01); *B29L 2031/4878* (2013.01)

(56) References Cited

U.S. PATENT DOCUMENTS

| | | | |
|---|---|---|---|
| 7,449,084 B2 * | 11/2008 | Nakakado | A61F 13/15739 156/580.1 |
| 7,658,053 B2 * | 2/2010 | Honegger | B29C 65/02 53/374.5 |
| 9,186,845 B2 * | 11/2015 | Shimada | A61F 13/15739 |
| 2007/0251643 A1 | 11/2007 | Umebayashi et al. | |
| 2010/0116409 A1 | 5/2010 | Yamamoto | |
| 2013/0008132 A1 | 1/2013 | Voegler et al. | |

FOREIGN PATENT DOCUMENTS

| | | |
|---|---|---|
| JP | 4592690 | 9/2010 |
| JP | 2013-522135 | 6/2013 |

* cited by examiner

ULTRASONIC HORN, WELDER PROVIDED THEREWITH, AND METHOD OF PRODUCING DISPOSABLE DIAPER USING ULTRASONIC HORN

TECHNICAL FIELD

The present invention relates to an ultrasonic horn that is used in ultrasonic welding, a welder provided with the ultrasonic horn, and a method of producing a disposable diaper using the ultrasonic horn.

BACKGROUND ART

Conventionally known disposable diapers include disposable diapers that include a front abdominal section disposed on the abdomen of the wearer, a rear dorsal section disposed on the buttocks of the wearer, and a crotch section that extends from the front abdominal section, passing between the legs of the wearer, up to the rear dorsal section.

In this disposable diaper, both side edges of the front abdominal section and both side edges rear dorsal section are welded to each other in such a manner that the front abdominal section and the rear dorsal section are connected in the form of a ring.

To produce a disposable diaper of this type, there is firstly prepared a continuous body in which constituent elements each constituted by connecting the front abdominal section and the rear dorsal section via the crotch section in the longitudinal direction are continuous in a transversal direction.

The continuous body is then folded in half in the longitudinal direction; in this state, an overlap portion of the front abdominal section and the rear dorsal section is ultrasonically welded, and the continuous body is cut in the transversal direction in such a manner that the resulting weld portions are present on both sides of the crotch section.

An ultrasonic horn that applies ultrasonic vibration to the continuous body having been folded in half is used herein for ultrasonic welding (see, for instance, Japanese Patent No. 4592690).

The continuous body includes a nonwoven fabric sheet, a waterproof sheet and an elastic body, and the thickness dimension of the overlap portion of the continuous body is large and uneven.

Accordingly, there is a demand for larger amplitudes (hereafter, output amplitude) of the ultrasonic vibration that is output by the ultrasonic horn, in order to generate effectively thermal energy, through ultrasonic vibration, in such an object to be welded.

SUMMARY OF INVENTION

It is an object of the present invention to provide an ultrasonic horn, the output amplitude of which can be increased, and to provide a welder provided with the ultrasonic horn, and a method of producing a disposable diaper using the ultrasonic horn.

In order to solve the above problem, the present invention provides an ultrasonic horn that is used in order to ultrasonically weld an object to be welded, the ultrasonic horn including: an input-side end section having an input surface that receives ultrasonic vibration; and an output-side end section having output surfaces which are disposed spaced apart from the input surface, by a distance corresponding to a half-wavelength of the ultrasonic vibration, and through which ultrasonic vibration is output to the object to be welded, wherein the output-side end section has a dimension, in a length direction, over which the object to be welded can be welded in a predetermined direction, and is branched in a width direction that is perpendicular to the length direction by a slit that extends in the length direction, and a pair of end faces of the output-side end section, positioned on both sides of the slit, functions as the output surfaces.

The present invention further provides an ultrasonic welder that includes the ultrasonic horn and an ultrasonic vibrator that generates mechanical vibration that is input to the ultrasonic horn.

The present invention provides also a method of producing a disposable diaper using the ultrasonic horn, the disposable diaper having a front abdominal section disposed on the abdomen of a wearer, a rear dorsal section disposed on the buttocks of the wearer, and a crotch section that extends from the front abdominal section, passing between the legs of the wearer, up to the rear dorsal section, the method including: a preparation step of preparing a continuous body in which constituent elements each constituted by connecting the front abdominal section and the rear dorsal section via the crotch section in a longitudinal direction are continuous in a transversal direction; a fold-in-half step of folding the continuous body in half in the longitudinal direction; a welding step of simultaneously welding two sites of the continuous body, by input of ultrasonic vibration to an input surface of the ultrasonic horn, in a state where a pair of output surfaces of the ultrasonic horn abuts an overlap portion in which a portion corresponding to a side edge portion of the front abdominal section and a portion corresponding to a side edge portion of the rear dorsal section are overlapped each other, in the continuous body; and a cutting step of cutting the continuous body between the two weld sections formed in the welding step.

The present invention allows increasing output amplitude.

DESCRIPTION OF EMBODIMENTS

The embodiments of the present invention are described hereinbelow by referring to the attached figures. The following embodiments are examples substantiating the present invention and do not limit the technical scope of the present invention.

Figure 1:
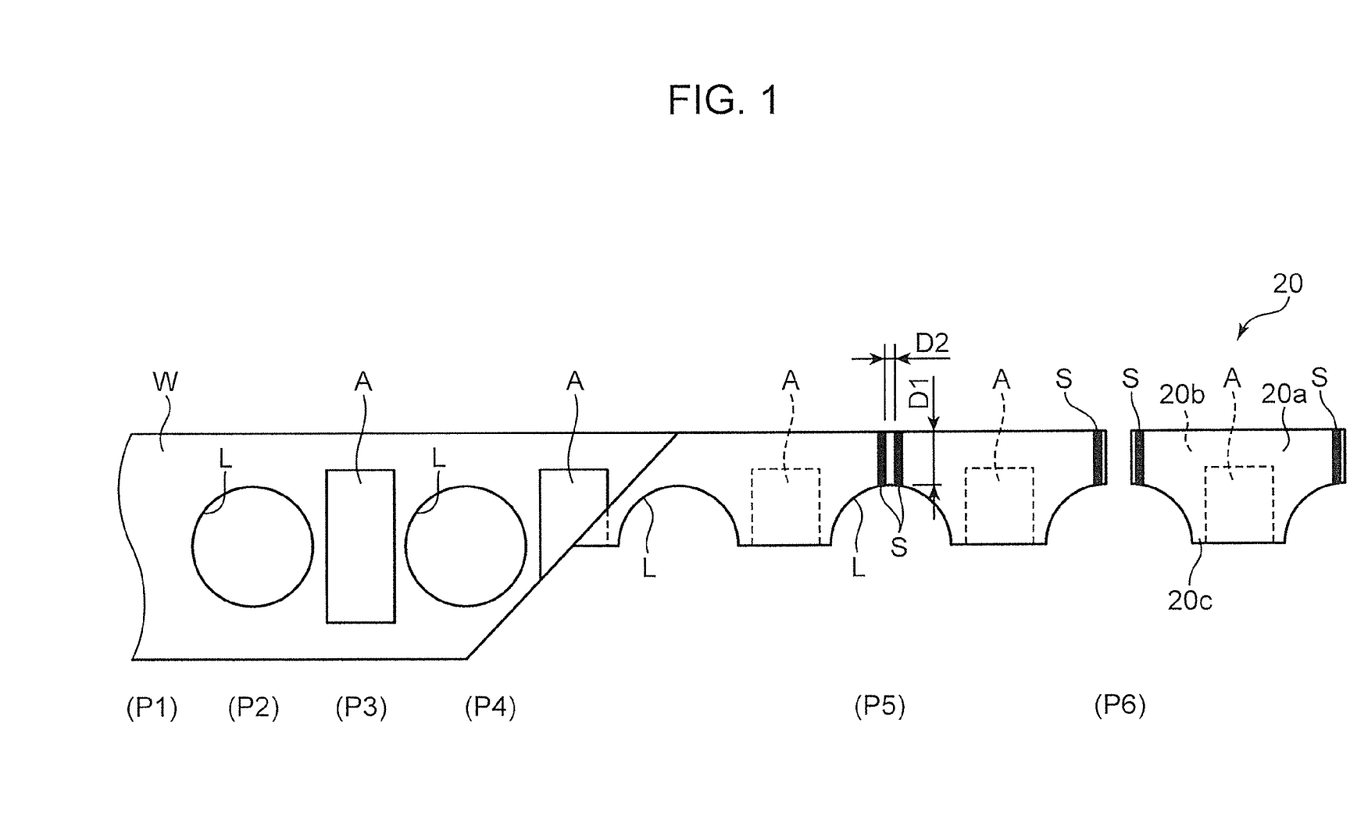
FIG. 1 is a process diagram for explaining a method of producing a disposable diaper according to the present invention.

With reference to FIG. 1, a disposable diaper 20 includes, when worn, a front abdominal section 20a disposed on the abdomen of the wearer, a rear dorsal section 20b disposed on the buttocks of the wearer, and a crotch section 20c that extends from the front abdominal section 20a, passing between the legs of the wearer, up to the rear dorsal section 20b.

Both side edge portions of the front abdominal section 20a and both side edge portions of the rear dorsal section 20b are welded to each other by two weld sections S, in such a manner that the front abdominal section 20a and the rear dorsal section 20b are connected in the form of a ring.

A method of producing the disposable diaper 20 will be explained next.

<Transport Step P1>

In the transport step P1, a sheet W that extends in a specific direction is transported along the length direction of the sheet W. In the explanation hereafter, the flow direction of the sheet W will be referred to as transversal direction, and the direction perpendicular to the transversal direction in FIG. 1 will be referred to as longitudinal direction.

The sheet W has an inner sheet that faces the body surface of the wearer when the wearer wears the diaper, an outer sheet that faces away from the wearer when the wearer wears the diaper, and an elastic member that is sandwiched between the inner sheet and the outer sheet.

The inner sheet is constituted by a nonwoven fabric sheet and/or a mesh sheet having liquid permeability. The outer sheet is constituted by a material, identical to that of the inner sheet, a polyethylene film, a polypropylene film, or a nonwoven fabric having water repellency and breathability.

The elastic member is constituted by a sheet or thread made of polyurethane, natural rubber, or a thermoplastic resin.

<Leg Hole Forming Step P2>

In the leg hole forming step P2, leg holes L are formed at a central position of the sheet W in the longitudinal direction.

Each region between the two leg holes L in the sheet W is a portion corresponding to the crotch section 20c. The positions on both sides of each portion in the sheet W corresponding to the crotch section 20c, in the longitudinal direction, correspond herein to the front abdominal section 20a and the rear dorsal section 20b, respectively.

That is, the transport step P1 and the leg hole forming step P2 correspond to the preparation step of preparing a continuous body (object to be welded) in which constituent elements each constituted by connecting the front abdominal section 20a and the rear dorsal section 20b via the crotch section 20c in the longitudinal direction are continuous in the transversal direction.

<Absorbent Body Bonding Step P3>

In the absorbent body bonding step P3, an absorbent body A is bonded at a position in the sheet W between the two leg holes L.

The absorbent body A includes a permeable sheet having liquid permeability, a water-repellent sheet having water-repellency and breathability, and an absorbent core sandwiched between the permeable sheet and the water-repellent sheet.

The permeable sheet is constituted by a nonwoven fabric sheet and/or a mesh sheet having liquid permeability. The water-repellent sheet is constituted by a polyethylene film, a polypropylene film, or a nonwoven fabric having water-repellency and breathability.

The absorbent core is molded through layering of crushed pulp or crushed pulp mixed with a high water-absorbing polymer.

A method is explained herein where the absorbent body A is bonded to the sheet W, but the absorbent core may be bonded in a state where the absorbent core is sandwiched between the inner sheet and the outer sheet of the sheet W. In this case, the inner sheet is constituted by a nonwoven fabric sheet and/or a mesh sheet having liquid permeability. The outer sheet is constituted by a polyethylene film, a polypropylene film, or a nonwoven fabric having water-repellency and breathability.

<Fold-in-Half Step P4>

In the fold-in-half step P4, the sheet W (continuous body) having the absorbent body A placed thereon is folded in half in the longitudinal direction. As a result, the portion of the sheet W corresponding to the front abdominal section 20a and the portion corresponding to the rear dorsal section 20b are overlapped each other.

<Welding Step P5>

In the welding step P5, a portion of the folded sheet W corresponding to a side edge portion of the front abdominal section 20a and the portion corresponding to a side edge portion of the rear dorsal section 20b are ultrasonically welded.

In the welding step P5, specifically, two sites of the sheet W are ultrasonically welded simultaneously, with a spacing that is wider than a predetermined cutting range D2 (for instance, 10 mm) as a range of cutting in the cutting step P6 described below.

The two weld sections S are respectively formed, over an entire range D1 in the longitudinal direction, of a portion corresponding to a side edge portion of the front abdominal section 20a, and a portion corresponding to a side edge portion of the rear dorsal section 20b.

<Cutting Step P6>

In the cutting step P6, the sheet W is cut along a respective cutting line that extends, in the longitudinal direction, between two weld sections S formed in the welding step P5. The sheet W (continuous body) is cut as a result into each disposable diaper 20.

Figure 2:
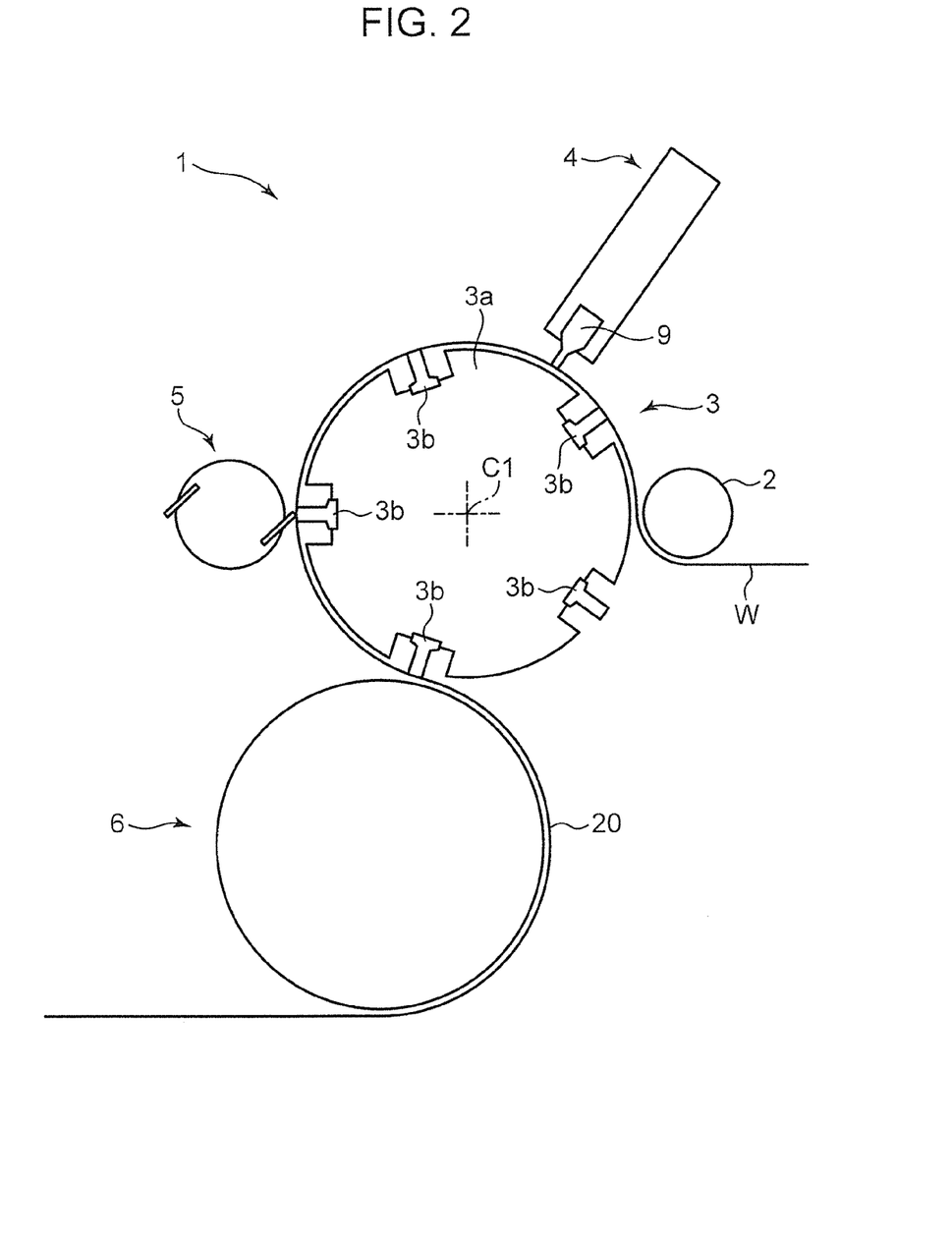
FIG. 2 is a side-view diagram illustrating a schematic configuration of a welding device according to a first embodiment, for performing a welding step and a cutting step illustrated in FIG. 1.

An explanation follows next, with reference to FIG. 2, on a welding device 1, according to the first embodiment, that carries out the welding step P5 and the cutting step P6.

The welding device 1 includes an introduction roller 2 that introduces the sheet W undergone the fold-in-half step P4; a drum 3 that transports the sheet W introduced by the introduction roller 2; a welder 4 that welds the sheet W between the drum 3 and the welder 4; a rotary cutter 5 that cuts the sheet W between the drum 3 and the rotary cutter 5; and a lead-out roller 6 that leads the sheet W out of the drum 3.

The drum 3 can rotate counter-clockwise, in FIG. 2, about a rotation center C1. The drum 3 includes a drum body 3a having an outer peripheral surface onto which the sheet W can be sucked, and five anvils 3b that are provided in recesses sunk from the outer peripheral surface of the drum body 3a, and that support, from inward, the sheet W that is sucked onto the drum body 3a.

The anvils 3b are disposed at equal intervals about the rotation center C1.

The welder 4 is provided outward of the drum 3 so as to sandwich the sheet W between the welder and the drum 3.

The sheet W is ultrasonically welded between the welder 4 and the sequentially opposing anvils 3b in response to the rotation of the drum 3.

The configuration of the welder 4 will be explained next with reference to FIG. 3.

The welder 4 includes an ultrasonic wave oscillator 12 that generates high-frequency electrical energy, an ultrasonic vibrator 7 that converts the electrical energy output by the ultrasonic wave oscillator 12 to mechanical vibration and that outputs the mechanical vibration, an amplifier 8 that is connected to the ultrasonic vibrator 7 and that amplifies the ultrasonic vibration input from the ultrasonic vibrator 7, and an ultrasonic horn 9 connected to the amplifier 8 and receiving the ultrasonic vibration from the amplifier 8.

The amplifier 8 has an input surface and an output surface that are spaced apart from each other by a distance corresponding to the half-wavelength of the ultrasonic vibration that is input from the ultrasonic vibrator 7. The input surface is connected to the ultrasonic vibrator 7, and the output surface is connected to the ultrasonic horn 9.

Figure 3:
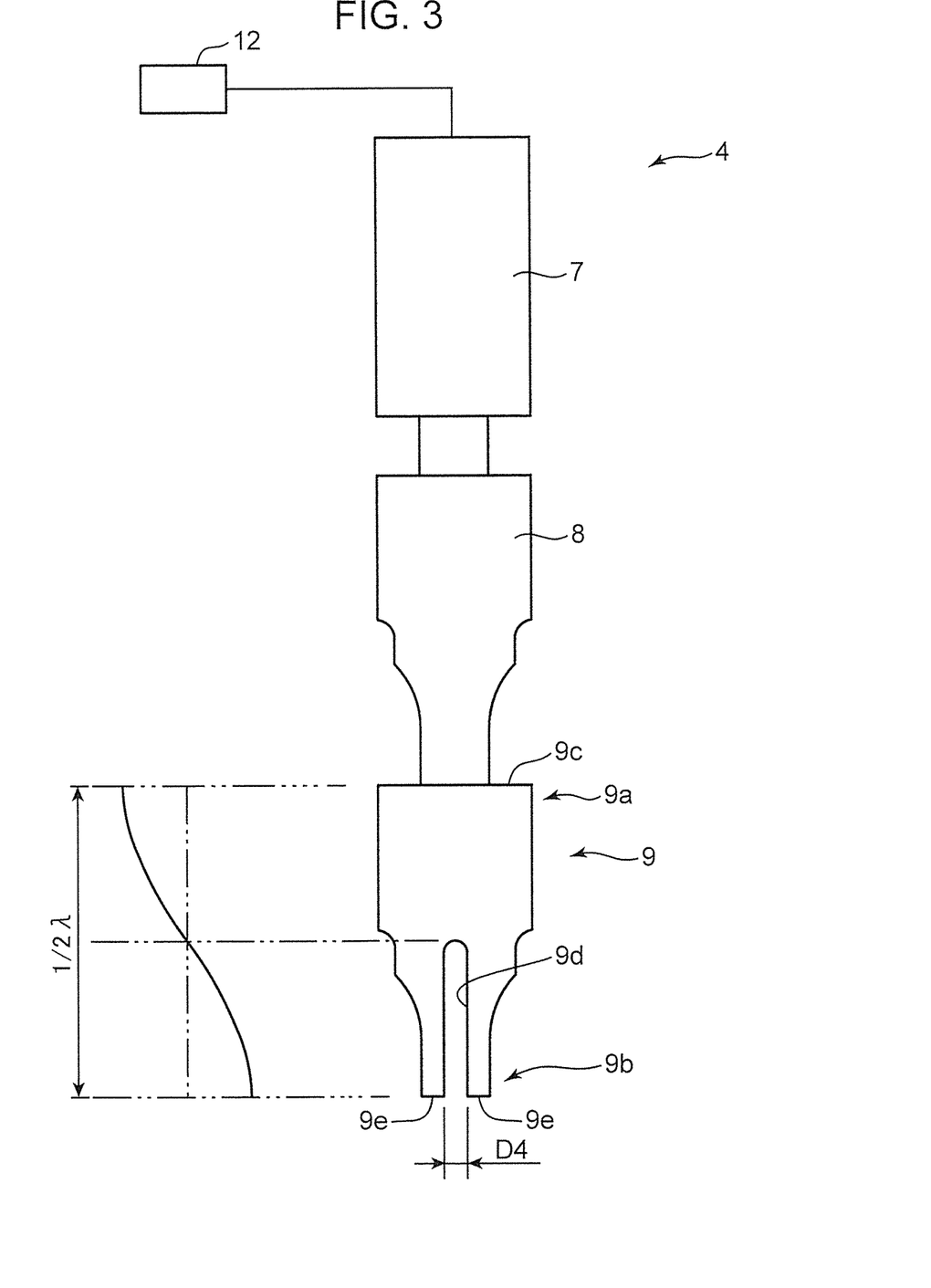
FIG. 3 is a front-view diagram illustrating an enlargement of the welder of FIG. 2.
Figure 4:
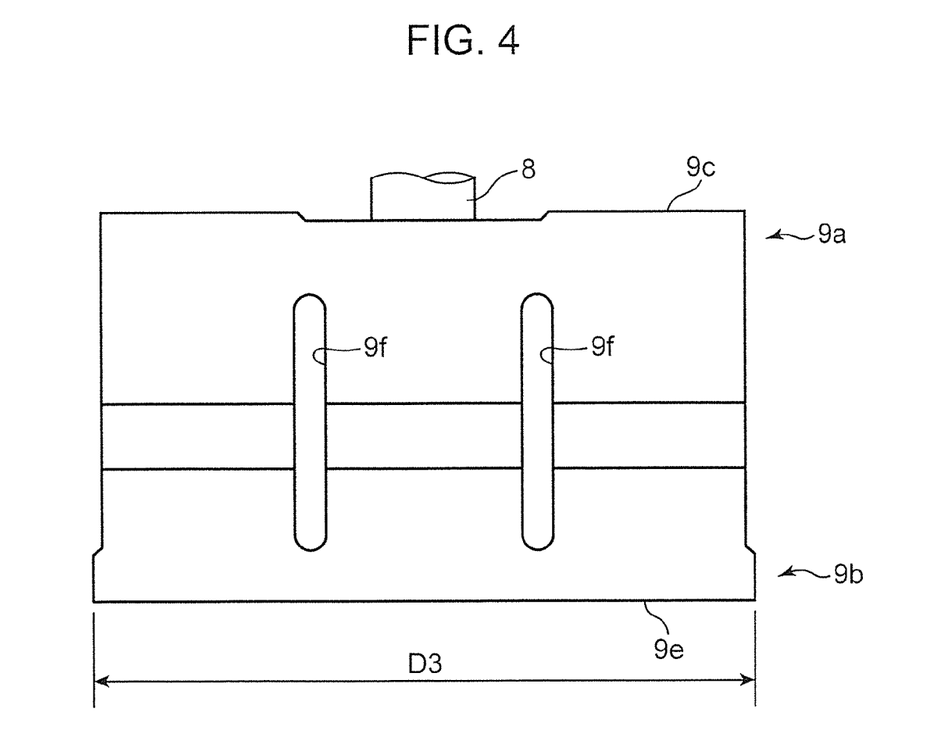
FIG. 4 is a side-view diagram of an ultrasonic horn illustrated in FIG. 3.

With reference to FIG. 3 and FIG. 4, the ultrasonic horn 9 includes an input-side end section 9a having an input surface 9c that receives the ultrasonic vibration from the amplifier 8, and an output-side end section 9b having a pair of output surfaces 9e which is disposed spaced apart from the input surface 9c by a distance corresponding to the half-wavelength (½λ) of the ultrasonic vibration that is input to the input surface 9c, and which outputs ultrasonic vibration to the sheet W.

The ultrasonic vibration that is input to the ultrasonic horn 9 are longitudinal waves in a direction perpendicular to the output surfaces 9e, but in the graph of FIG. 3, the ultrasonic vibration is depicted as a transverse wave, for convenience in the explanation.

The output-side end section 9b has a dimension D3 (left-right direction in FIG. 4) over which the entire range D1 (see FIG. 1), in the longitudinal direction, of the portion of the sheet W corresponding to a side edge portion of the front abdominal section 20a, and the portion of the sheet W corresponding to a side edge portion of the rear dorsal section 20b can be welded.

The output-side end section 9b is branched in the width direction (left-right direction in FIG. 3), perpendicular to the length direction, by a slit 9d that extends in the length direction. That is, the pair of output surfaces 9e is constituted by end faces of the output-side end section 9b, split by the slit 9d. The width dimension of the pair of output surfaces 9e is, for instance, 12 mm.

Herein, the width dimension of slit 9d is set to a dimension D4 (spacing between the output surfaces 9e: for instance, 12 mm), wider than the cutting range D2 (see FIG. 1) for cutting the sheet W in the transversal direction.

In the above example, an instance has been explained where the width dimension of the cutting range D2 is 10 mm, and the width dimension D4 of the slit 9d is 12 mm. The smaller the width dimension of the slit 9d, the smaller can be made the pitch of the disposable diaper 20; accordingly, the width dimension of the cutting range D2 can be set for instance to 6 mm, and the width dimension D4 of the slit 9d can be set to 8 mm.

The width dimension D4 of the slit 9d can be made smaller than the width dimension of the cutting range D2. In this case, however, the weld section is present at the cut surface, and the end face of the disposable diaper 20 becomes hard and exhibits a unattractive appearance. Accordingly, the width dimension D4 of the slit 9d is preferably set to be larger than the width dimension of the cutting range D2, as described above.

The slit 9d is formed over a range from a position corresponding to a node of the ultrasonic vibration that is input through the input surface 9c, up to the end face (output surfaces 9e) of the output-side end section 9b.

The ultrasonic horn 9 has a shape so as to taper off, in the width direction, toward the output surfaces 9e, from a position corresponding to the node of the ultrasonic vibration that is input through the input surface 9c.

The purpose of the pair of through-holes 9f that extend in the up-down direction and are disposed spaced apart from each other in the left-right direction, in FIG. 4, is to adjust the transmission of ultrasonic vibration that is output from the output surfaces 9e in such a manner that the ultrasonic vibration becomes homogeneous in the length direction (left-right direction in FIG. 4) of the output surfaces 9e. The through-holes 9f communicate with the slit 9d.

The rotary cutter 5 has a roller that can rotate about an axis parallel to the rotation center C1, and a cutting blade provided on the outer peripheral surface of the roller. The sheet W is cut between the cutting blade and each anvil 3b when the cutting blade and the anvil 3b oppose each other, in response to the rotation of the roller and the drum body 3a.

With reference to FIG. 1 and FIG. 3, in a case where the welding step P5 is carried out using the welding device 1, ultrasonic vibration is input to the input surface 9c of ultrasonic horn 9, in a state where the pair of output surfaces 9e of the ultrasonic horn 9 abuts the overlap portion in which the portion corresponding to a side edge portion of the front abdominal section 20a and the portion corresponding to a side edge portion of the rear dorsal section 20b in the sheet W are overlapped each other.

As a result, it becomes possible to weld simultaneously two sites of the sheet W between the ultrasonic horn 9 and each anvil 3b (see FIG. 2).

A portion of the sheet W between the two weld sections S thus formed is cut between the rotary cutter 5 and each anvil 3b (cutting step P6).

As explained above, the slit 9d extending in the length direction is formed in the output-side end section 9b, and the spacing between the pair of output surfaces 9e positioned on both sides of the slit 9d is set to be larger than the cutting range D2.

As a result, the output amplitude can be increased through a reduction in the mass of the output-side end section 9b, by virtue of the slit 9d, and it becomes possible to use, as the cutting range D2, the non-welding area of the sheet W defined by the slit 9d.

Therefore, the present invention allows welding, simultaneously and reliably, two sites of the folded portion of the sheet W (weld sites of two adjacent disposable diapers 20).

The following effects can be obtained according to the above embodiment.

In the above embodiment, the output-side end section 9b has the length dimension D3 over which the side edge portions of the front abdominal section 20a and the side edge portions of the rear dorsal section 20b can be welded over the entire range D1 in the longitudinal direction. Accordingly, the output amplitude can be increased, as described above, while securing the function of welding the sheet W in the entire range D1.

In the embodiment, the output amplitude can be increased reliably by reducing the weight of the ultrasonic horn 9 only at the portion thereof that is closer to the output surfaces 9e than the node of ultrasonic vibration is.

In particular, the slit 9d is formed over a range from the position corresponding to the node of ultrasonic vibration up to the end face of the output-side end section 9b. Reduction of the weight of the ultrasonic horn by the slit 9d can be maximized as a result.

Figure 5:
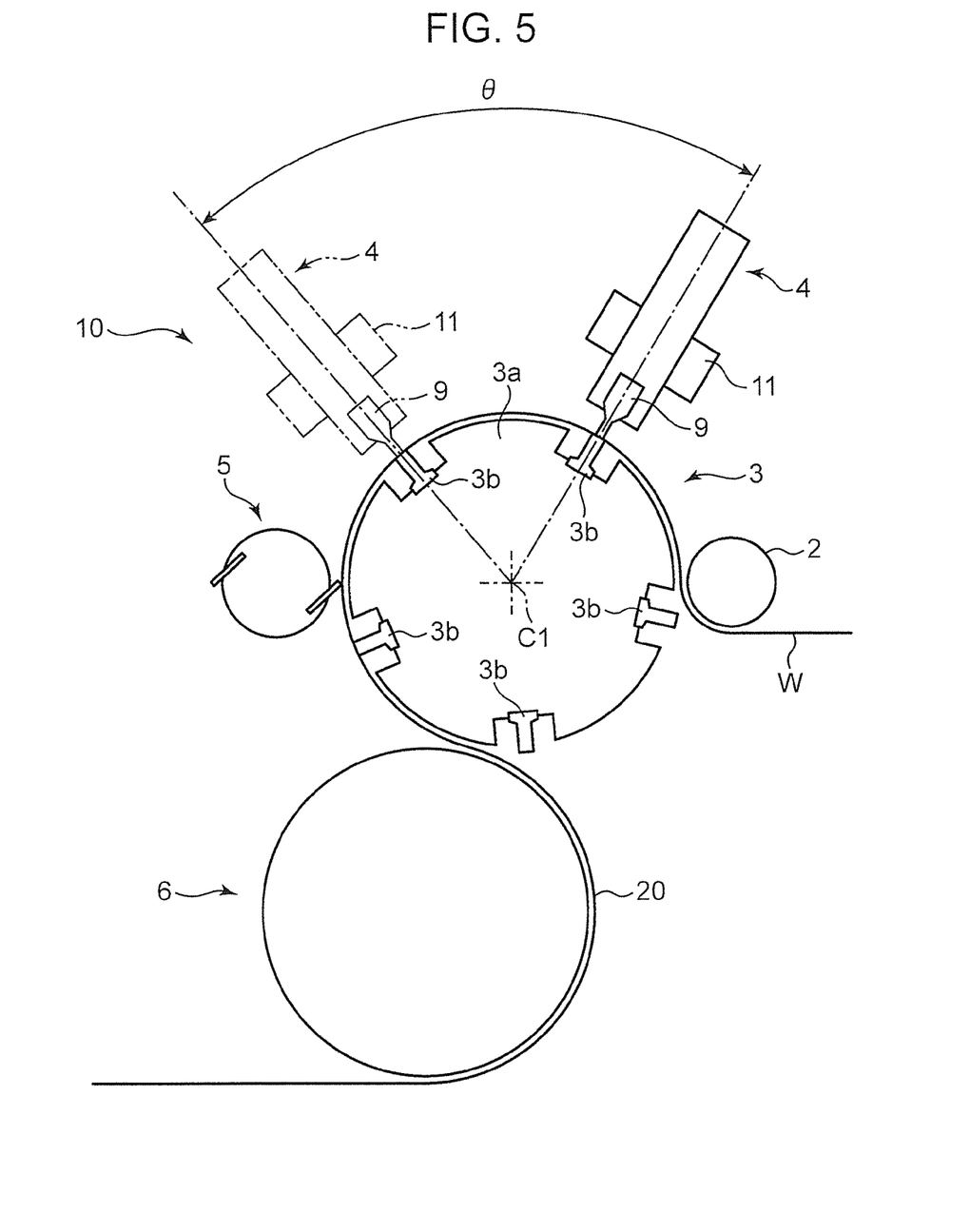
FIG. 5 is a side-view diagram illustrating the schematic configuration of a welding device according to a second embodiment of the present invention.

A welding device 10 according to a second embodiment will be explained next with reference to FIG. 5. Features identical to those of the welding device 1 according to the first embodiment will be denoted by identical reference symbols, and an explanation thereof will be omitted.

The welding device 10 has a holding section 11 that can rotate about the rotation center C1, together with the drum 3, and that holds the welder 4 slidably in a direction along the rotation center C1.

In order to avoid contact with the introduction roller 2, the rotary cutter 5 and the lead-out roller 6, the holding section 11 is provided at a position at which the holding section 11 avoids the introduction roller 2, the rotary cutter 5 and the lead-out roller 6, in a direction along the rotation center C1.

The welder 4 is held in the holding section 11 in such a manner that the welder 4 slides to welding positions opposing respective anvils 3b, within an angle range θ about the rotation center C1, and slides to an avoidance position where the welder 4 avoids the introduction roller 2, the rotary cutter 5 and the lead-out roller 6, within an angle range other than the angle range θ.

Specifically, the welder 4 is connected to the drum 3, via a cam mechanism not shown, in such a manner that the welder 4 slides between the welding position and an avoidance position, in response to the rotation of the drum 3.

Therefore, the welding device 10 allows utilizing, as a welding period, the period during which the drum 3 rotates over the angle range θ, and hence the sheet W can be welded yet more reliably.

In a case where the sheet W is cut downstream of the welding device 10 (case where the rotary cutter 5 is not provided in the drum 3), the anvils 3b can be caused to slide in synchrony with the sliding of the welder 4, between the welding position and the avoidance position.

The welder 4 can be provided inside the drum 3, and the anvils 3b outside the drum 3, and at least one of the welder 4 and the anvils 3b can be caused to slide.

A third embodiment of the present invention will be explained next with reference to FIG. 6 to FIG. 8.

In a welding device 30 of the third embodiment, the ultrasonic horns 9 are provided inside a rotary drum 35 (side close to the center), and anvils 38 are provided outside the rotary drum 35 (far side from the center), such that the anvils 38 can slide with respect to the ultrasonic horns 9.

The purpose of the welding device 30 is to ultrasonically weld the sheet W that is introduced via an introduction roller 50 after being folded in half in the fold-in-half step P4, and to feed the welded sheet W to the cutting step P6, via a lead-out roller 51.

Figure 6:
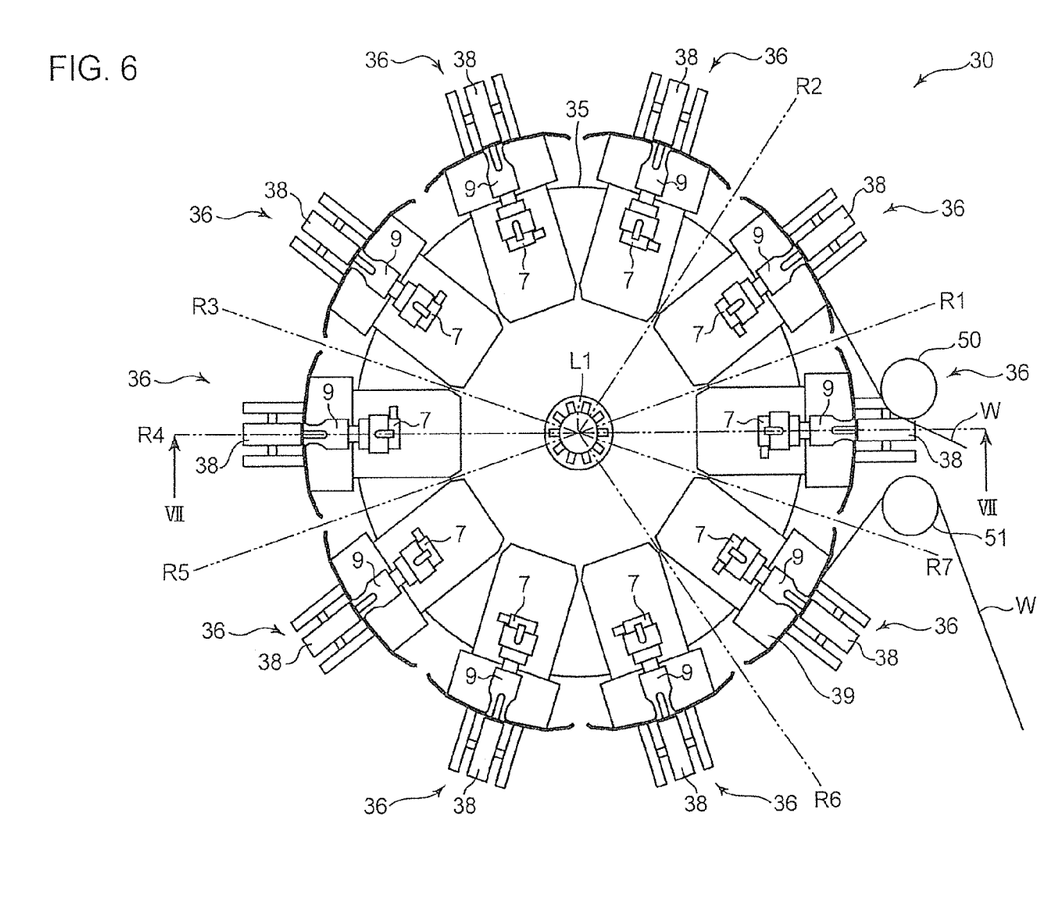
FIG. 6 is a front-view diagram illustrating a welding device according to a third embodiment of the present invention.
Figure 7:
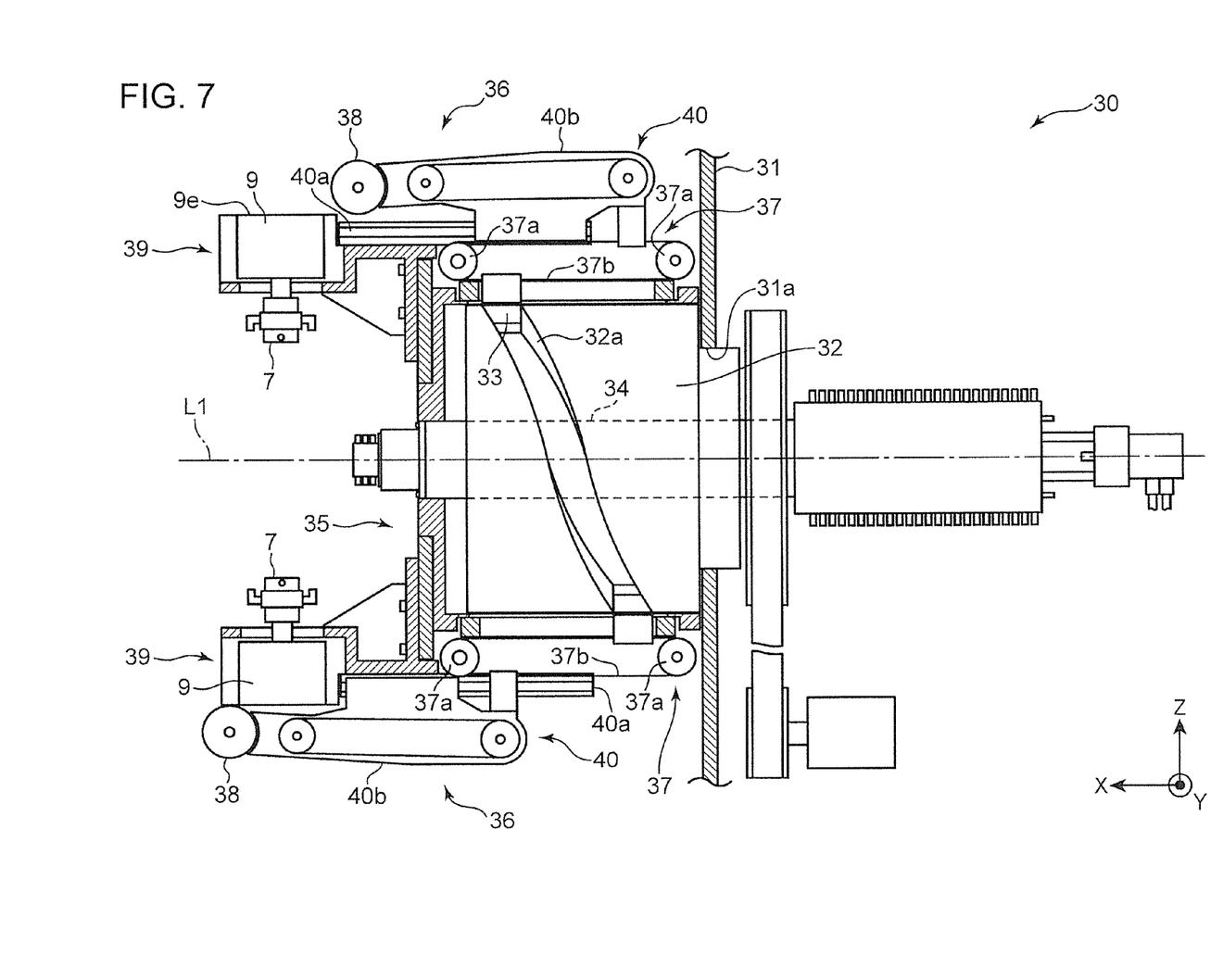
FIG. 7 is a cross-sectional diagram along line VII-VII of FIG. 6.

As illustrated in FIG. 6 and FIG. 7, specifically, the welding device 30 includes a drive shaft support member 31, a cam drum 32 fixed to the drive shaft support member 31, a cam follower 33 provided inside a cam groove 32a of the cam drum 32, a drive shaft 34 rotatably supported with respect to the drive shaft support member 31 about a rotation axis L1, the rotary drum 35 fixed to the drive shaft 34, ten welding units 36 fixed to the rotary drum 35, and ten power transmission mechanisms 37 for transmitting power from the cam drum 32 and the cam follower 33 to the welding units 36.

In the explanation below, the direction parallel to the rotation axis L1 in FIG. 6 will be set as the X direction, the up-down direction in FIG. 6 as the Z direction, and the direction perpendicular to the X-Z plane as the Y direction.

The cam drum 32 is fixed to the drive shaft support member 31 in a state where one end of the cam drum 32, in the X direction, is engaged with a through-hole 31a of the drive shaft support member 31. In this state, the axis of the cam drum 32 coincides with the rotation axis L1.

The cam groove 32a is formed on the outer peripheral surface of the cam drum 32. The cam groove 32a, which is described below in detail, has a shape that allows the cam follower 33, which rotates about the rotation axis L1, to move in the X direction.

The drive shaft 34 penetrates through the cam drum 32 in the X direction, in a state where the drive shaft 34 can rotate relatively with respect to the cam drum 32. Specifically, the drive shaft 34 is supported on the drive shaft support member 31 indirectly, via the cam drum 32.

The rotary drum 35 is fixed to the leading end section, of the drive shaft 34, that protrudes out of the cam drum 32. The rotary drum 35 rotates about the rotation axis L1 in response to the rotation of the drive shaft 34. The rotary drum 35 is a cylindrical drum that covers the outer peripheral surface of the cam drum 32.

The ten welding units 36 are fixed to the rotary drum 35 in a state where the welding units 36 are disposed equidistantly (at 36° intervals) about the rotation axis L1. The configurations of the ten welding units 36 are identical, and, accordingly, the configuration of just one welding unit 36 will be explained next.

Each welding unit 36 has the ultrasonic horn 9 and the anvil 38 that sandwich the sheet W and weld the sheet W, the ultrasonic vibrator 7 that is connected to the ultrasonic horn 9, a horn holding mechanism 39 that is fixed to the rotary drum 35 and that holds the ultrasonic horn 9, and an anvil holding mechanism 40 that is fixed to the rotary drum 35 and that holds the anvil 38.

The anvil 38 is a rotatably-supported roller-like member that slides with respect to the ultrasonic horn 9, as described below, so that, as a result, the anvil 38 can come into rolling contact with the sheet W that is supported on the ultrasonic horn 9.

Figure 8:
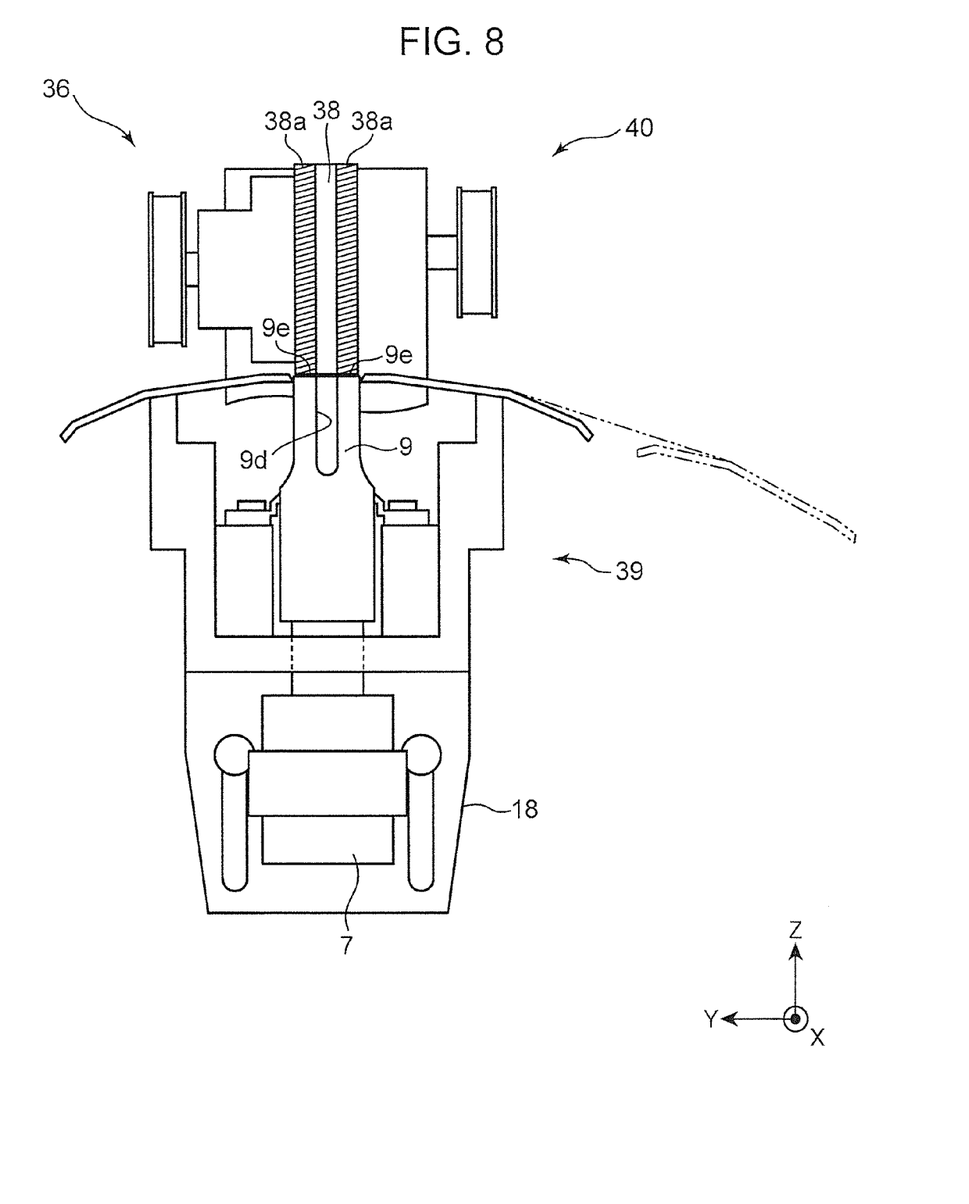
FIG. 8 is an enlarged-view diagram of a welding unit illustrated in FIG. 6.

As illustrated in FIG. 8, two welding patterns 38a are formed on the outer peripheral surface of the anvil 38, at positions opposing the two output surfaces 9e of the ultrasonic horn 9. The welding patterns 38a are constituted by a plurality of protrusions that protrude from the outer peripheral surface of the anvil 38 outward in the radial direction. The overlap portion in the sheet W can be welded intermittently by the plurality of protrusions.

The protrusions extend parallelly to each other and obliquely with respect to a direction that is parallel to the rotation axis of the anvil 38. As a result, the contact pressure (contact surface area) of the anvil 38 with the output surfaces 9e (sheet W) is rendered substantially uniform regardless of the rotational position of the anvil 38.

With reference to FIG. 7 and FIG. 8, the horn holding mechanism 39 holds the ultrasonic horn 9 in a state where the output surfaces 9e of the ultrasonic horn 9 face outward in the radial direction of the rotary drum 35.

The anvil holding mechanism 40 holds the anvil 38 in such a manner that the anvil 38 can move, in the X direction, with respect to the horn holding mechanism 39 (ultrasonic horn 9). As illustrated in FIG. 7, specifically, each anvil holding mechanism 40 includes a rail 40a that is fixed to the rotary drum 35 and that extends in the X-axis direction, and a holding section 40b that is slidably attached to the rail 40a along the X-axis direction, and that holds the anvil 38.

Each power transmission mechanism 37 connects the cam follower 33 and the holding section 40b in such a manner that the holding section 40b of the anvil holding mechanism 40 moves in the X-axis direction in response to the movement of the cam follower 33.

Specifically, the power transmission mechanism 37 includes a pair of timing pulleys 37a, and a timing belt 37b that is looped around the timing pulleys 37a. The cam follower 33 is fixed to one of the two portions, of the timing belt 37b, between the timing pulleys 37a, while the holding section 40b of the anvil holding mechanism 40 is fixed to the other of the two portions.

As a result, the anvil holding mechanism 40 moves, in the X direction, in an direction opposite to the cam follower 33, when the cam follower 33 moves toward one side in the X direction.

The range of movement of the anvils 38 is set by the cam groove 32a as follows.

The anvils 38 can move over a range of movement between an initial position (position depicted at the top in FIG. 7) that is spaced apart from the ultrasonic horn 9 toward the cam drum 32 in the X direction, to an intermediate position (position depicted at the bottom of FIG. 7) that is spaced apart from the ultrasonic horn 9 toward the side opposite to the cam drum 32 in the X direction.

The relationship between the rotational position about the rotation axis L1 and the movement position of the anvil 38 is set, as described below, by the cam groove 32a.

As illustrated in FIG. 6, the introduction roller 50 and the lead-out roller 51 are disposed between rotational position R1 and rotational position R7 about the rotation axis L1. The anvils 38 are disposed at the initial position (position depicted at the top of FIG. 7), within a range from rotational position R7 to rotational position R1.

In the range from rotational position R1 to rotational position R2, the anvils 38 accelerates from the initial position toward the intermediate position (hereafter, this orientation will be referred to as forward). In the range from rotational position R2 to rotational position R3, the anvils 38 move forward at constant speed. During this movement the sheet W is welded between the ultrasonic horns 9 and the anvils 38.

In the range from rotational position R3 to rotational position R4, the anvils 38 decelerate (rearward acceleration is imparted to the anvils 38), so that the anvils 38 stop at an intermediate position (position depicted at the bottom of FIG. 7), at rotational position R4.

In the range from rotational position R4 to rotational position R5, the anvils 38 accelerate rearward, from the intermediate position toward the initial position.

In the range from rotational position R5 to rotational position R6, the anvils 38 move rearward at constant speed. During this movement the sheet W is welded again between the ultrasonic horns 9 and the anvils 38.

In the range from rotational position R6 to rotational position R7, the anvils 38 decelerate (forward acceleration is imparted to the anvils 38), so as to stop at the initial position, at rotational position R7.

In the above embodiments, as illustrated in FIG. 3, the slit 9d extends from a position corresponding to a node of the ultrasonic vibration, toward the end face of the output-side end section 9b (output surfaces 9e). If the slit 9d extends toward the end face of the output-side end section 9b from a position that is closer to the output surfaces 9e than the node is, it becomes possible to reduce the ratio of the mass of the ultrasonic horn 9 on the output surfaces 9e side from the node, to the mass of the ultrasonic horn 9 on the input surface 9c side from the node, and to increase thus the output amplitude.

In the above embodiments, the amplifier 8 is provided between the ultrasonic vibrator 7 and the ultrasonic horn 9, but the amplifier 8 can be omitted, since the output amplitude can be increased by virtue of the slit 9d, as described above.

That is, the ultrasonic vibrator 7 can be connected directly to the input surface 9c of the ultrasonic horn 9.

The ultrasonic welder can be made more compact as a result.

In the above embodiments, the output-side end section 9b has a length dimension D3 over which the entire range D1, in the longitudinal direction, of the side edge portions of the front abdominal section 20a and the side edge portions of the rear dorsal section 20b can be welded but the output-side end section 9b may have a length dimension such that only part of the entire range D1 is weldable.

In the above embodiments an ultrasonic horn 9 for welding the continuous body of the disposable diaper 20 is explained, but the object to be welded is not limited to being a continuous body of a disposable diaper.

The specific embodiments described above include an invention having the following features.

Specifically, the present invention provides an ultrasonic horn that is used in order to ultrasonically weld an object to be welded, the ultrasonic horn including: an input-side end section having an input surface that receives ultrasonic vibration; and an output-side end section having output surface which is disposed spaced apart from the input surface, by a distance corresponding to a half-wavelength of the ultrasonic vibration, and through which ultrasonic vibration is output to the object to be welded, wherein the output-side end section has a dimension, in a length direction, over which the object to be welded can be welded in a predetermined direction, and is branched in a width direction that is perpendicular to the length direction by a slit that extends in the length direction, and a pair of end faces of the output-side end section, positioned on both sides of the slit, functions as the output surface.

As is known, the output amplitude of an ultrasonic horn generally increases with decreasing ratio of the mass of the ultrasonic horn in a portion on the output surface side with respect to the mass of a portion on the input surface side, with reference to a node of the ultrasonic vibration that is input.

The output-side end section having the output surface can be conceivably made smaller thus in the length direction. However, there are limits to reducing the output-side end section in the length direction, since the output-side end section has to have a longitudinal dimension that enables welding of the object to be welded, over a wide area, along a predetermined direction.

In the present invention, therefore, a slit extending in the length direction is formed in the output-side end section, and the spacing between the pair of end faces (output surface) positioned on both sides of the slit is set to be larger than the cutting range.

As a result, the present invention allows increasing the output amplitude by reducing the mass of the output-side end section by the slit.

Preferably, in order to produce a disposable diaper that has a front abdominal section disposed on the abdomen of a wearer, a rear dorsal section disposed on the buttocks of the wearer, and a crotch section that extends from the front abdominal section, passing between the legs of the wearer, up to the rear dorsal section, the ultrasonic horn is used in order to ultrasonically weld an overlap portion in which a portion corresponding to a side edge portion of the front abdominal section and a portion corresponding to a side edge portion of the rear dorsal section are overlapped each other, in a state where a continuous body, in which constituent elements each constituted by connecting the front abdominal section and the rear dorsal section via the crotch section in a longitudinal direction are continuous in a transversal direction, is folded in half in the longitudinal direction, the output-side end section has a dimension, in the length direction, over which the side edge portion of the front abdominal section and the side edge portion of the rear dorsal section can be welded along the longitudinal direction, and the pair of end faces of the output-side end section positioned on both sides of the slit are disposed at a spacing larger than a predetermined cutting range as a range for cutting the continuous body along a cutting line that extends in the longitudinal direction.

This aspect allows utilizing a non-welding area of the continuous body, defined by the slit, as the cutting range, while increasing the output amplitude by a reduction in the mass of the output-side end section by the slit, as described above.

Therefore, two sites of the overlap portion of the continuous body (weld sites of two adjacent the disposable diapers) can be welded simultaneously and reliably, such that a disposable diaper can be produced by cutting the continuous body between the weld portions.

In the ultrasonic horn, preferably, the output-side end section has a dimension, in the length direction, over which the side edge portion of the front abdominal section and the side edge portion of the rear dorsal section can be welded over an entire range thereof in the longitudinal direction.

This aspect allows increasing the output amplitude, as described above, while securing the function of welding the entire range, in the longitudinal direction, of the side edge portion of the front abdominal section and the side edge portion of the rear dorsal section.

In the ultrasonic horn, preferably, the slit is formed over a range extending from a position corresponding to a node of ultrasonic vibration, or a position that is closer to the output surface than the position corresponding to the node of ultrasonic is, up to the end faces of the output-side end section.

In this aspect, the output amplitude can be increased reliably by reducing the weight of the ultrasonic horn only at the portion thereof that is closer to the output surface than the node of ultrasonic vibration is.

In particular, the reduction in the weight of the ultrasonic horn afforded by the slit can be maximized in a case where the slit is formed over an area from the position corresponding to the node of ultrasonic vibration up to the end face of the output-side end section.

The "node" is a position at which the amplitude of the waveform of ultrasonic vibration becomes minimum (0).

The present invention further provides an ultrasonic welder that includes the ultrasonic horn and an ultrasonic vibrator that generates mechanical vibration that is input to the ultrasonic horn.

In the ultrasonic welder, preferably, the ultrasonic vibrator is directly connected to an input surface of the ultrasonic horn.

In the ultrasonic horn, specifically, the output amplitude can be increased by the slit, and, accordingly, it becomes possible to omit an amplifier for amplifying the ultrasonic vibration from the ultrasonic vibrator. The ultrasonic welder can be made more compact as a result.

This does not mean however that the present invention excludes the feature of providing an amplifier between the ultrasonic horn and the ultrasonic vibrator.

The present invention also provides a method of producing a disposable diaper using the ultrasonic horn, the disposable diaper having a front abdominal section disposed on the abdomen of a wearer, a rear dorsal section disposed on the buttocks of the wearer, and a crotch section that extends from the front abdominal section, passing between the legs of the wearer, up to the rear dorsal section, the method including: a preparation step of preparing a continuous body in which constituent elements each constituted by connecting the front abdominal section and the rear dorsal section via the crotch section in a longitudinal direction are continuous in a transversal direction; a fold-in-half step of folding the continuous body in half in the longitudinal direction; a welding step of simultaneously welding two sites of the continuous body, by input of ultrasonic vibration to an input surface of the ultrasonic horn, in a state where a pair of output surfaces of the ultrasonic horn abuts an overlap portion in which a portion corresponding to a side edge portion of the front abdominal section and a portion corresponding to a side edge portion of the rear dorsal section are overlapped each other, in the continuous body; and a cutting step of cutting the continuous body between the two weld sections formed in the welding step.

The production method according to the present invention allows welding a continuous body in a state where the output amplitude has been increased by the use of an ultrasonic horn having a slit, and allows cutting a continuous body at a non-welding area (area between the two weld sections), defined by the slit, of the continuous body.

Therefore, the production method according to the present invention allows welding, simultaneously and reliably, two sites of the overlap portion of the continuous body, and cutting the continuous body between the weld sites, to produce thereby a disposable diaper.

The invention claimed is:

1. An ultrasonic horn that is used in order to ultrasonically weld an object to be welded, comprising:
   an input-side end section having an input surface that receives ultrasonic vibration; and
   an output-side end section having output surface which is disposed spaced apart from the input surface, by a distance corresponding to a half-wavelength of the ultrasonic vibration, and through which ultrasonic vibration is output to the object to be welded,
   wherein the output-side end section has a dimension, in a length direction, over which the object to be welded can be welded in a predetermined direction, and is branched in a width direction that is perpendicular to the length direction by a slit that extends in the length direction,
   a pair of end faces of the output-side end section, positioned on both sides of the slit, functions as the output surface,
   the slit is formed over a range extending from a position corresponding to a node of ultrasonic vibration, or a position that is closer to the output surface than the position corresponding to the node of ultrasonic vibration and extends to the end faces of the output-side end section, and
   the slit has a depth of one-eighth or more wavelength of ultrasonic vibration.

2. The ultrasonic horn according to claim 1,
wherein, in order to produce a disposable diaper that has a front abdominal section disposed on the abdomen of a wearer, a rear dorsal section disposed on the buttocks of the wearer, and a crotch section that extends from the front abdominal section, passing between the legs of the wearer, up to the rear dorsal section, the ultrasonic horn is used in order to ultrasonically weld an overlap portion in which a portion corresponding to a side edge portion of the front abdominal section and a portion corresponding to a side edge portion of the rear dorsal section are overlapped each other, in a state where a continuous body, in which constituent elements each constituted by connecting the front abdominal section and the rear dorsal section via the crotch section in a longitudinal direction are continuous in a transversal direction, is folded in half in the longitudinal direction, the output-side end section has a dimension, in the length direction, over which the side edge portion of the front abdominal section and the side edge portion of the rear dorsal section can be welded along the longitudinal direction, and the pair of end faces of the output-side end section positioned on both sides of the slit are disposed at a spacing larger than a predetermined cutting range as a range for cutting the continuous body along a cutting line that extends in the longitudinal direction.

3. The ultrasonic horn according to claim 2, wherein the output-side end section has a dimension, in the length direction, over which the side edge portion of the front abdominal section and the side edge portion of the rear dorsal section can be welded over an entire range thereof in the longitudinal direction.

4. An ultrasonic welder, comprising:
the ultrasonic horn according to claim 1 and
an ultrasonic vibrator that generates mechanical vibration that is input to the ultrasonic horn.

5. The ultrasonic welder according to claim 4, wherein the ultrasonic vibrator is directly connected to an input surface of the ultrasonic horn.

6. A method of producing a disposable diaper using the ultrasonic horn according to claim 2, the disposable diaper having a front abdominal section disposed on the abdomen of a wearer, a rear dorsal section disposed on the buttocks of the wearer, and a crotch section that extends from the front abdominal section, passing between the legs of the wearer, up to the rear dorsal section, the method comprising:
a preparation step of preparing a continuous body in which constituent elements each constituted by connecting the front abdominal section and the rear dorsal section via the crotch section in a longitudinal direction are continuous in a transversal direction;

a fold-in-half step of folding over the continuous body in the longitudinal direction;

a welding step of simultaneously welding two sites of the continuous body, by input of ultrasonic vibration to an input surface of the ultrasonic horn, in a state where a pair of output surfaces of the ultrasonic horn abuts an overlap portion in which a portion corresponding to a side edge portion of the front abdominal section and a portion corresponding to a side edge portion of the rear dorsal section are overlapped each other, in the continuous body; and a cutting step of cutting the continuous body between the two weld sections formed in the welding step.

* * * * *